United States Patent [19]

Diamond

[11] Patent Number: 4,690,905
[45] Date of Patent: Sep. 1, 1987

[54] METHOD FOR REMOVAL OF HUMAN ANTIBODIES TO NATIVE DNA FROM SERUM

[75] Inventor: Betty A. Diamond, New York, N.Y.

[73] Assignee: Albert Einstein College of Medicine of Yeshiva University, a division of Yeshiva University, Bronx, N.Y.

[21] Appl. No.: 556,588

[22] Filed: Nov. 30, 1983

Related U.S. Application Data

[63] Continuation-in-part of Ser. No. 552,290, Nov. 16, 1983, which is a continuation-in-part of Ser. No. 446,718, Dec. 3, 1982, abandoned.

[51] Int. Cl.[4] .................. G01N 33/564; G01N 33/577
[52] U.S. Cl. ..................................... 436/508; 210/635; 210/656; 210/927; 435/172.2; 436/529; 436/538; 436/540; 436/542; 436/545; 436/548; 436/811; 436/824; 530/387; 530/813; 530/808; 935/108; 935/110
[58] Field of Search ................... 424/85; 436/506, 507, 436/508, 529, 538, 540, 542, 545, 548, 804; 435/172.2; 935/89, 93, 95, 96, 99, 100, 104, 106, 110; 210/635, 656, 927; 260/112 B; 530/387

[56] References Cited

U.S. PATENT DOCUMENTS

| 4,490,290 | 12/1984 | Gani et al. | 260/112 B |
| 4,493,899 | 1/1985 | Smith et al. | 436/508 |
| 4,544,640 | 10/1985 | Soma et al. | 436/506 |

FOREIGN PATENT DOCUMENTS

WO80/00026  1/1980  World Int. Prop. O. .......... 436/508

OTHER PUBLICATIONS

Köhler, G., and Milstein, C., Nature, vol. 256, 495–497 (1975).
Andrzejewski, C., Rauch, J., Lafer, E., Stollar, B. D., and Schwartz, R. S., Journal of Immunology, vol. 126, 226–231 (1981).
Abdov, N. I., Wall, H., Lindsley, H. B., Halsey, J. F., and Suzuki, T., Journal of Clinical Investigation, vol. 67, 1297–1304 (1981).
Joyce Rausch et al., "A High Frequency Idiotypic Mark etc", The Journal of Immunology, vol. 129, No. 1, Jul. 1982.
Betty Diamond et al., "Reactivity of Monoclonal Anti Idiotype etc", Biological Abstracts/RRM No. 26051813, from Clin. Res., vol. 31, No. 2, p. 520 A, 1983.
G. A. Solomon et al., "The Use of Mono Clonal Anti Idiotypic etc", Biological Abstracts RRM, No. 26023959, from Clin. Res., vol. 31, No. 1, p. 161A, 1983.

*Primary Examiner*—Christine M. Nucker

[57] ABSTRACT

The invention relates to monoclonal anti-idiotypic antibodies to human anti-DNA antibodies. Monoclonal, anti-idiotypic antibodies are produced using hybridoma technology. The antibodies are used as diagnostic reagents in methods to determine the presence of anti-native DNA antibodies in serum from patients suspected of having systemic lupus erythematosus, and as therapeutic reagents in methods to remove the anti-native DNA antibodies from the serum of patients with systemic lupus erythematosus.

9 Claims, No Drawings

METHOD FOR REMOVAL OF HUMAN ANTIBODIES TO NATIVE DNA FROM SERUM

RELATED APPLICATIONS

This application is a continuation-in-part of application Ser. No. 552,290, filed Nov. 16, 1983, which in turn is a continuation-in-part of application Ser. No. 446,718, filed Dec. 3, 1982, abandoned.

BACKGROUND OF THE INVENTION

The present invention relates to monoclonal antibodies capable of reacting with shared idiotypes on human anti-native DNA antibodies. The invention also relates to diagnostic test methods to detect the presence of anti-native DNA antibodies in patients suspected of having systemic lupus erythematosus, and to therapeutic uses involving methods for removing the anti-native DNA antibodies from the serum of patients with systemic lupus erythematosus.

The term "antibody" as used in immunology is a generic term and is used to cover numerous immunoglobulin molecules which may be alike in some respects and different in other respects. Antibodies sharing a common effector function are referred to as isotypes and include the major immunoglobulin classes IgA, IgD, IgE, IgG and IgM, each of which is constructed from a heavy polypeptide chain characteristic of the particular class and a light polypeptide chain (either kappa or lambda), the heavy and light chains being joined by disulfide bridges. Heterologous antibodies, i.e. those raised in one species against the antibodies of another species, are useful in recognizing isotypes.

Antibodies of a given isotype, e.g. IgG, can be subdivided further on the basis of the particular type of heavy chain from which they are composed, e.g. $\gamma 1$, $\gamma 2$, $\gamma 3$, etc. Antibodies having the same general type of heavy chain can still show some heterogeneity in the heavy chain. Within a given animal species, certain regions on the heavy chain of a given isotype may be the same or different. Those antibodies showing similarity within these regions are referred to as allotypes. The similarity is believed to be of genetic origin.

Finally, antibodies of a given isotype and allotype may differ on the basis of their structure in or near their antigen binding regions (Fab region). Antibodies showing similarlity in this region are said to be of the same idiotype. Particular discrete antigenic sites within these regions are referred to as idiotypic determinants or frequently just idiotypes. Antibodies having common or shared idiotypes generally have the same antigenic specificity.

Despite common antigenic specificity among idiotypes, not all idiotypic determinants are located in the antigen binding site of an immunoglobulin molecule. This has been demonstrated by the fact that a second antibody directed against an idiotypic determinant on the first antibody (the second antibody being referred to hereinafter as an anti-idiotypic antibody) and the antigen do not always compete for the antigen binding site on the first antibody. Idiotypic determinants are controlled by both genetic and antigenic influences. Antibodies from genetically different individuals which share a common antigenic specificity usually exhibit idiotypic heterogeneity. That is, even though the antibodies are capable of binding the same antigen, the structure of idiotypic determinants, even when located in the antigen binding site, are different.

Antibodies directed against idiotypic determinants on immunoglobulin molecules provide unique probes for detecting antibodies associated with and characteristic of auto-immune diseases. Serum containing anti-idiotypic antibodies has been used to demonstrate shared idiotypes on immunoglobulins from unrelated patients in a number of auto-immune disease including myasthenia gravis, Graves Disease, cold agglutinin disease, and rheumatoid arthritis. Antibodies to native DNA (anti-nDNA) produced by inbred mice with diseases resembling human systemic lupus erythematosus (SLE) have been shown to share a common idiotype, but shared idiotypy has not previously been demonstrated in the anti-nDNA antibodies of human patients with SLE.

Systemic lupus erythematosus is a disease which is being diagnosed with ever-increasing frequency. A minimal estimate of its incidence is 10 per 100,000 people, but it occurs preferentially in blacks and in women of child-bearing age. Its incidence in family members of patients with SLE is at least one hundred fold greater than its incidence in the population at large, but the genetics of inheritance remain unclear. Systemic lupus erythematosus is a disease of protean manifestations both clinically and serologically. Clinically, SLE can affect any organ system. It causes constitutional systems such as fever and malaise. It causes arthritis, serositis (plural, peritoneal, and pericardial), renal disease, hematologic abnormalities, and central nervous system disturbances. The sera from lupus patients are capable of reacting with a variety of antigens due to the presence of auto-antibodies. These antibodies are directed primarily against nuclear antigens and cell membrane antigens, although some antibodies to cytoplasmic antigens have been described. The auto antibody which is specific for SLE and most commonly found in the serum from SLE patients is antibody to native DNA.

Attempts to remove these pathogenic anti-native DNA antibodies from the serum of patients with SLE normally result in a generalized immunosuppression. At present, treatment for the SLE patient affects the patient's ability to generate any and all antibodies. The removal of all antibodies from the serum of a patient results in a generalized immunosuppression. This "suppression" of all immune responses is highly undesirable as it leaves the SLE patient in a weakened state, unable to fight off infections and other diseases.

As stated earlier, one individual generally produces many different antibodies against a given antigen such as DNA. While all such antibodies are capable of reacting with the common antigen, the antibodies may exhibit structural differences, thereby imparting idiotypic heterogeneity. Furthermore, additional idiotypic difference will generally exist between antibodies produced by genetically nonidentical individuals against a common antigen. Consequently, one would expect that in the genetically diverse human population, there would be wide heterogeneity in anti-DNA antibodies from patients with SLE. Therefore, an anti-idiotypic antibody produced against an anti-DNA antibody from one individual would not be expected to cross react with anti-DNA antibodies from other genetically nonidentical individuals within the population. In the present invention, monoclonal anti-idiotypic antibodies have been produced against the anti-native DNA antibodies from one SLE patient which, unexpectedly, do cross react with anti-nDNA antibodies from genetically nonidentical SLE patients within the human population. This unexpected cross-reactivity allows these monoclonal antibodies to be used as diagnostic reagents to detect anti-nDNA antibody in serum from suspected SLE patients within the population at large. In addition, this cross-reactivity allows these monoclonal antibodies to be used in a therapeutic modality involving the removal of antinDNA antibodies from the serum of SLE patients.

DISCLOSURE OF THE INVENTION

In one aspect, the present invention is a composition of matter comprising monoclonal antibodies capable of reacting with shared idiotypes on human anti-native DNA antibody (also referred to herein as monoclonal, anti-idiotypic antibody).

In another aspect, the present invention is a method for detecting anti-native DNA suspected of being present in a liquid biological sample, comprising contacting the sample with monoclonal, anti-idiotypic antibodies capable of binding to shared idiotypes on human anti-native DNA antibody, and determining the extent of binding.

In still another aspect, the present invention is a method for removing anti-native DNA antibodies present in a liquid biological sample, comprising contacting the sample with a medium containing monoclonal, anti-idiotypic antibodies capable of binding to shared idiotypes on human anti-native DNA antibody, and separating the medium from the sample to remove the human anti-native DNA antibody therefrom.

In a further aspect, the present invention is a therapeutic modality involving the removal of anti-native DNA antibodies from the serum of patients with SLE.

DETAILED DESCRIPTION OF THE INVENTION

The anti-idiotypic antibody of the present invention is monoclonal (derived from a single hybridoma) and is of either the IgG or IgM isotype, the former being preferred. Additionally, the antibody is not reactive with nonidiotypic regions of normal human immunoglobulin. The antibody can bind to an idiotypic determinant located in the antigen binding region of the anti-nDNA antibody or to an idiotypic determinant located outside the antigen binding region, the latter being preferred because of the ability of the monoclonal antibody to detect circulating immune complexes. The antibody cross reacts with idiotypes shared between two or more genetically nonidentical individuals.

The monoclonal, anti-idiotypic antibodies of this invention can be made using known cell fusion techniques. See, for example, Gefter et al., Somatic Cell Genet., Volume 3, pp 231-236 (1977) and Kearney et al., J. Immunol., Volume 123, pp 1548-1550 (1979). In general, a B lymphocyte from a mammalian organism (human or nonhuman) which has been specifically sensitized to anti-native DNA antibodies from an organism of either the same or different species as that from which the lymphocyte is obtained is fused with a compatible fusion partner which is preferably a nonsecreting myeloma cell line. The resulting fusion products are then screened for those hybridomas which secrete antibody which meets the criteria set forth above. The selected hybridomas can then be expanded by known techniques including passage as ascites.

In a preferred embodiment, the specifically sensitized B cell is made as follows. Serum from an SLE patient is reacted with DNA, generally from an extraneous source such as calf thymus. An immune complex of DNA and anti-DNA is allowed to form. The complex is isolated using, for example, ion exchange chromatography, and dissociated, generally by treatment with 8M urea. This anti-DNA antibody is then recovered using, for example, DEAE-cellulose chromatography. An alternate method for obtaining purified human anti-nDNA antibody comprises the generation of a human x human hybridoma which secretes anti-nDNA antibody. A preferred method for generating such a hybridoma is the fusion of peripheral blood lymphocytes from an SLE patient whose serum contains high levels of anti-DNA antibody with a drug marked human myeloma cell line. After fusion, the hybridoma supernatant fluid can be screened for anti-DNA antibody using conventional assays such as the Millipore filter assay described below. The recovered anti-DNA antibody produced by either of these methods is then used as an immunogen to sensitize B lymphocytes in an immunocompetent recipient animal, generally a mouse. A preferred strain of mouse is BALB/c. After immunization, the mouse is sacrificed and splenocytes recovered for fusion with appropriate fusion partners. A preferred fusion partner for a sensitized mouse splenocyte is the non secreting, thioguanineresistant myeloma line X63Ag8.653 which is on deposit at the American Type Culture Collection (Rockville, Md., U.S.A.) and catalogued as ATCC CRL-1580. Following fusion of lymphocyte and fusion partner to produce hybridomas, hybridoma supernatant fluids are screened for the presence of antibody capable of reacting with antiDNA antibody. A preferred method of screening is a sandwich solid phase radioimmunoassay in which hybridoma supernatant fluid is contacted with a solid phase having coated thereon anti-DNA antibody (normal human immunoglobulin is used as a control). Any antibody in the supernatant fluid capable of binding to antigenic determinants on the anti-DNA antibody will be absorbed onto the solid phase. Finally, a labeled antibody directed against nonidiotypic determinants on the hybridoma produced antibody is contacted with the solid phase and the extent of immunospecific binding determined by means of the label which can be an enzyme, radioisotope, chromophore, fluorophore, etc. To distinguish hybridoma supernatant fluids containing antibody directed against isotypic and allotypic determinants on the anti-DNA antibody from supernatant fluids containing antibody directed against idiotypic determinants, the amount of immunospecifically adsorbed label on solid phase precoated with anti-DNA antibody is compared to the amount of immunospecifically adsorbed label on solid phase pre-coated with normal human immunoglobulin (control). Hybridoma supernatant fluids accounting for greater immunospecific label adsorption on solid phase precoated with normal human immunoglobulin are considered to contain anti-idiotypic antibody. Those supernatant fluids which account for approximately equal or greater label adsorption on solid phase pre-coated with normal human immunoglobulin as compared to solid phase pre-coated with anti-DNA antibody are considered to contain antiisotypic and/or antiallotypic antibody. To determine whether the anti-idiotypic antibody is capable of reacting with shared idiotypes, the screening described above can be repeated using anti-DNA antibody from at least two genetically nonidentical individuals. Hybridoma supernatant fluids showing reactivity with at least two anti-DNA antibodies are considered as capable of reacting with a shared idiotype on human anti-native DNA antibody and, therefore, within the scope of the present invention.

Because of their ability to detect circulating immune complexes of DNA and anti-native DNA in patient serum, the most preferred antibody of the present invention is one which is capable of reacting with a shared idiotypic determinant on human anti-native DNA antibody which is located outside the DNA binding region. Hybridomas secreting this most preferred antibody can be identified by reacting anti-DNA antibody and hybridoma supernatant fluid prescreened for anti-idiotype activity in the presence of a large excess of free DNA. If the binding of the monoclonal antibody in the supernatant fluid and the anti-DNA antibody is not inhibited, the monoclonal antibody may be directed against an idiotypic determinant on anti-DNA antibody located outside of the DNA binding site. To further demonstrate that the putative monoclonal anti-idiotypic antibody is not binding to DNA, itself, a coprecipiation assay can be performed. In this assay, radiolabeled, generally Iodine-125 labeled, DNA is incubated with anti-DNA antibody or a negative control, the former preferably from an SLE patient with high titer anti-nDNA activity and the latter from a non-SLE control patient. The amounts of radiolabeled DNA and anti-nDNA antibody are chosen to avoid precipitate formation. Next supernatant fluid pre-screened for anti-idiotypic activity or a control, preferably supernatant fluid from a mouse myeloma cell line secreting a monoclonal antibody of the same isotype as the anti-idiotypic antibody, but which is nonreactive with human immunoglobulin, is added. Finally, a heterologous antiserum capable of reacting with both the monoclonal antiidiotypic antibody and the antibody control is added in an amount capable of forming an immune precipitate. The precipitate is washed and the amount of radioactivity is determined. If the amount of radioactivity in the precipitate containing the putative monoclonal anti-idiotypic antibody and the anti-DNA antibody is greater than that of the controls, it can be concluded that the monoclonal antibody does not bind DNA directly.

After the identification and selection of hybridomas which secrete monoclonal antibodies capable of reacting with shared idiotypes on human anti-native DNA antibody, the selected hybridomas can be cloned. A preferred method of cloning comprises depositing the selected hybridoma cells on agarose on a feeder layer of rat embryo fibroblasts, growing the cells to mass culture, retesting for anti-idiotypic activity, and, finally, injecting recipient animals peritoneally and tapping ascites. A preferred animal is a pristane-primed BALB/c mouse.

It is hypothesized that SLE patients secreting high levels of anti-DNA antibody will also produce auto-antibodies directed against their own anti-DNA antibodies. It is predicted that such auto-antibodies would reduce the levels of circulating anti-DNA in the serum of such patients. It would be possible to produce a human, monoclonal antibody capable of reacting with a shared idiotype on human anti-nDNA antibody by direct fusion of peripheral blood lymphocytes from an SLE patient in serological remission (namely, when levels of circulating anti-nDNA antibody are low) with a drug marked human myeloma cell. The supernatant fluid of a hybridoma so produced would be screened for human, monoclonal anti-idiotypic antibody by the following screening procedure. A solid phase, generally the well of a microtiter plate is coated with purified Fab fragments of human anti-DNA antibody. Solid phase coated with purified Fab fragments of normal human immunoglobulin is used as a control. Hybridoma supernatant fluid is contacted with the solid phases and unadsorbed fluid washed away. Finally, the solid phases are contacted with a labeled heterologous antibody specific for the Fc region of human immunoglobulin. Greater binding of label to the solid phase coated with Fab fragments of human anti-DNA as compared to the control is evidence of the presence of monoclonal antiidiotypic antibody. To determine whether the anti-idiotypic antibody is capable of reacting with shared idiotypes, the screening procedure is repeated using anti-DNA antibody from at least two genetically nonidentical individuals. Hybridoma supernatant fluids showing reactivity with at least two anti-DNA antibodies are considered as capable of reacting with a shared idiotype on human antinative DNA antibody, and, therefore, within the scope of the present invention.

The antibody of the present invention can be used to detect the presence of anti-nDNA antibody in biological fluids by a variety of techniques which are well known in the art. In all of these techniques, the monoclonal, anti-idiotypic antibody of this invention is contacted with a sample suspected of containing anti-nDNA and the amount of binding determined. Among the suitable techniques are radioimmunoassay (RIA, solid or liquid phase), enzyme-linked immunosorbent assay, heterogeneous immunoassay (both competitive and noncompetitive) using labels other than enzymes and radioisotopes, homogeneous immunoassays based on fluorescence quenching and enzyme channeling, immune precipitation (including radial immune diffusion) and agglutination assays based on visual semiquantitative detection or quantitative turbidimetric detection. In one preferred mode, the monoclonal, anti-idiotypic antibody is used in a liquid phase RIA in which a labeled monoclonal, anti-idiotypic antibody is reacted with a sample whereby immune complex forms. The label can be a radioisotope such as Iodine-125 or an enzyme such as horseradish peroxidase, $\alpha$-galactosidase or alkaline phosphatase. After a suitable reaction time, a reagent capable of precipitating the immune complex is added. A preferred reagent is a heterologous antibody reactive with the anti-nDNA antibody. The amount of label in the precipitate is determined and compared to positive and negative controls. A kit can be configured to contain the necessary reagents:

(i) anti-nDNA antibody positive and negative controls;

(ii) labeled monoclonal, anti-idiotypic antibody;

(iii) reagent capable of precipitating immune complexes of anti-nDNA antibody and monoclonal anti-idiotypic antibody; and (iv) directions for using the kit.

In another preferred mode, the test sample is coated on a solid phase such as the interior wall of a polystyrene test tube or microtiter plate well. After washing away unadsorbed sample, the solid phase is contacted with the monoclonal, anti-idiotypic antibody of this invention. After a suitable incubation perid, unreacted monoclonal antibody is washed away. Finally, the solid phase is contacted with an enzymatically labeled or radiolabeled heterologous antibody reactive with the monoclonal antibody. After a suitable incubation period, the unreacted labeled antibody is washed away, and the amount of immunospecifically adsorbed label measured. If the monoclonal antibody is of mouse origin, a preferred radiolabeled heterologous antibody is Sulfur-35-methionine labeled rate anti-mouse light chain antibody.

The antibody of the present invention can be used to remove anti-nDNA antibody from biological fluids, including the serum of SLE patients, by a variety of techniques. In these techniques, a medium containing the monoclonal, anti-idiotypic antibody of this invention is contacted with a sample containing anti-nDNA antibody so that binding occurs and the medium adsorbs the anti-nDNA antibody. The medium containing the anti-idiotypic antibody of the present invention and the anti-nDNA antibody is then separated from the sample to remove the anti-nDNA antibody therefrom. It will be appreciated that this medium may be either a solid or liquid phase. The removal of the anti-nDNA antibodies from the serum of a patient with SLE may result in the clinical remission of the disease and it is believed that the removal of the anti-nDNA antibodies is a viable therapeutic modality for patients with SLE. Further, the antibody of the present invention can also be used to remove circulating immune complexes of anti-nDNA antibody and DNA from the serum of SLE patients. Therapeutically, this is highly desirable as it is known that these immune complexes are a major pathogenic component of disease in SLE patients.

In one preferred mode, the monoclonal, anti-idiotypic antibody is coupled to sepharose to produce a separation medium which could be disposed in a column. Serum samples are applied to the column and the anti-nDNA antibody in the serum binds to the antiidiotypic antibody coupled to the sepharose in the column. The filtrate, which is depleted of anti-nDNA antibodies, is removed from the column. The serum sample can also be depleted of circulating immune complexes of anti-nDNA antibody and DNA if one uses the antibody of the present invention which is capable of reacting with a shared idiotypic determinant on human anti-nDNA antibody which is located outside the DNA binding region. Finally, the anti-nDNA antibody may be eluted from the column to permit reuse of the column.

EXAMPLE

Ten mL of serum from an SLE patient (A.W.) containing antiDNA antibodies was mixed with 10 mL of 0.01M Na phosphate buffer, pH 6.6, containing calf thymus DNA (Type 1, Sigma Chemical Co., St. Louis, Mo.) at a concentration of 1.5 mg/mL. This mixture was incubated for 1 hour at room temperature followed by 16 hours at 4° C. to allow DNA/anti-DNA antibody complexes to form and was then applied to a 300 mL DE-52 column (Whatman Ltd., Clifton, N.J.) equilibrated with 0.01M Na phosphate (pH 6.6) containing 0.1M NaCl. The complexes were eluted with 0.5M NaCl, dissociated with 8M urea and rechromatographed on a DE-52 column to yield an enriched preparation of human anti-DNA antibodies of the IgG class which were free of native DNA.

Five BALB/c mice were immunized by intraperitoneal injection with 100 μg of an immunogen which is the enriched anti-DNA antibody emulsified in complete Freund's adjuvant. The mice were boosted weekly for 6 to 10 weeks with the immunogen without adjuvant. Three of the five mice were shown, using a solid phase radioimmunoassay (see below), to have produced high levels of antibodies against the immunogen. Spleen cells from these three immunized mice were fused to thioguanine-resistant non immunoglobulin secreting, mouse myeloma cells (line X63Ag8.653) and plated in 96 well microtiter plates. Supernatant fluids from those cultures containing viable hybridomas were screened to detect clones producing antibodies reactive with purified immunogen using a solid phase radioimmunoassay. Samples of each culture supernatant fluid were incubated in wells of Immulon-II (Dynatech Labs., Inc., Alexandria, Va.) microtiter plates which had been precoated by overnight incubation with either purified anti-DNA antibodies from an SLE patient or with purified normal human immunoglobulin. After extensive washing of the coated plates, bound mouse immunoglobulin was detected by addition of a Sulfur-35-methionine labeled monoclonal rat anti-mouse kappa light chain antibody. Differential binding of radiolabel to the anti-DNA plate relative to the normal human immunoglobulin plate was taken as evidence for the presence of a putative anti-idiotypic antibody specific for anti-DNA in the culture supernatant fluid of a given hybridoma. Five of such hybridomas were identified as shown in Table I.

TABLE I

| Identification of hybridomas producing anti-idiotype | | |
|---|---|---|
| | Anti-DNA antibodies cpm | Control human serum, cpm |
| Positive control* | 15,226 | 8,554 |
| | 18,195 | 11,402 |
| Control** | 135 | 120 |
| | 112 | 109 |
| Hybridoma | | |
| 3I | 2,107 | 157 |
| | 1,885 | 135 |
| 9F | 2,255 | 154 |
| | 1,942 | 114 |
| 17A | 306 | 131 |
| | 332 | 211 |
| 3H | 223 | 124 |
| | 192 | 102 |
| 9E | 152 | 100 |
| | 160 | 99 |

*Serum from a mouse that had been immunized at a dilution of 1:100.
**Supernatant from an irrelevant hybridoma line.

Either enriched AW anti-DNA antibodies or control serum was absorbed to polystyrene wells. Mouse serum or hybridoma supernatant was added, followed by radiolabeled rat anti-mouse light chain. Duplicate values are shown.

Cells from these hybridomas were further cloned in agarose on a feeder layer of rat embryo fibroblasts. Clones were picked, grown to mass culture and retested for anti-idiotypic activity. Pristane-primed BALB/c mice were injected intraperitoneally with 1 ×10⁷ hybridoma cells, and the ascites fluid was harvested 10–14 days later.

The monoclonal antibody hereinafter designated 3I which was produced by one of these clones was further characterized as follows. Ouchterlony analysis indicated 3I to be a moust IgG1 immunoglobulin with kappa light chains. Activity of 3I against antiDNA antibodies was not inhibited by a fifty-fold excess of normal human serum. Furthermore, its binding to anti-DNA antibody was not blocked by the addition of a large excess of free DNA. 3I did not contain anti-DNA acitivity as measured in a conventional Millipore filter assay. (Iodine-125 labeled DNA is reacted with a dilution of serum suspected of containing anti-DNA antibody. Immune complex is trapped on a 0.45um filter which is then counted for radioactivity.) Furthermore, 3I antibody when combined with a rabbit anti-mouse antibody was capable of precipitating radiolabeled DNA only if the DNA had been preincubated with anti-DNA antibodies from patient sera. Finally, 3I was found to bind to the Fab region of anti-DNA antibodies.

From these data, it was concluded that the 3I antibody was anti-idiotypic and was specific for an idiotype present on a species of anti-DNA antibodies from patient AW. Furthermore, the 3I antibody is not directed against the antigen combing site of anti-DNA antibody because binding to anti-DNA is not blocked by the addition of excess DNA, and because it binds to DNA-/anti-DNA antibody complexes.

Sera obtained from active SLE patients and normal healthy donors were tested to determine their reactivity with 3I using a solid phase radioimmunoassay. In this assay, the sera, diluted 1/10 in phosphate buffered saline (PBS), were incubated overnight at 4° C. in the wells of an Immulon-II microtiter plate. Plates were washed three times with PBS and then incubated for 1 hours with PBS containing 5% (w/v) bovine serum albumin (BSA). Culture supernatant fluid or a 1/50 dilution of ascites containing 3I was added to each well. After 90 minutes incubation at room temperature, the plates were washed with a washing solution containing 0.5% Tween 20, 0.15M NaCl and 2% BSA (pH 8.3). Sulfur-35-methionine-labeled monoclonal rat anti-mouse kappa light chain antibody (clone 187.1, ATCC-HB 58) was added and the plates further incubated at room temperature for 90 minutes. After extensive washing with the washing solution, the extent of binding was determined in each well by scintillation counting.

Eight of nine active SLE patients previously shown to have high levels of anti-DNA antibodies showed significant reactivity with 3I. Furthermore, four of nine active patients without significant reactivity in the Millipore filter assay for anti-DNA antibodies also reacted with 3I. Many of these sera from patients with SLE reacted with 3I more strongly than did serum from patient AW, from which the anti-DNA antibody was purified. In contrast, none of the ten normal donors showed significant 3I-reactivity in their sera.

Serum samples were obtained from thirteen patients during active disease and during clinical remission. Remission sera from all patients showed a loss of anti-nDNA antibody in the Millipore filter assay. Six of these remission sera showed a concomitant loss of 3I reactivity in the solid phase radioimmunoassay. However, the remaining seven remission sera showed little or no change in 3I reactivity. The continued reactivity of these seven sera with 3I suggests that anti-nDNA antibodies were present, but were prevented from reacting with DNA in the Millipore filter assay. Therefore an assay for detecting anti-nDNA in serum samples using 3I as a reagent has greater diagnostic and prognostic utility than anti-nDNA assays of the prior art. The hybridoma secreting 3I has been deposited in accordance with the provisions of the Budapest Treaty at the American Type Culture Collection, Rockville, Md., where it is catalogued as ATCC HB8376.

The antibody of the present invention can be used to remove anti-nDNA antibody from biological fluids, including the serum of SLE patients, by contacting the serum to a medium containing the monoclonal, anti-idiotypic antibody of this invention. Specifically, cyanogen bromide was used to activate normally inert sepharose to permit the coupling of the antibody 3I to the sepharose. The sepharose was then placed in a suitable container to form a column. Serum samples from patients with SLE were then applied to this column so that the anti-nDNA in the serum binds to the 3I on the sepharose. The column was then washed with phosphate buffered saline to remove the serum from the column, this filtrate being depleted of anti-nDNA antibodies. The anti-nDNA antibody was then eluted from the column using 8M urea to dissociate the complex formed by the 3I and anti-nDNA antibodies, leaving the 3I in the column which may now be used again. This fraction containing the eluted anti-nDNA antibodies is then dialyzed against 6M urea, 4M urea, 2M urea and finally against phosphate buffered saline, leaving the fraction containing the eluted anti-nDNA antibody free of urea.

The filtrate (serum passed through the column) was then shown to be depleted of 3I reactive anti-nDNA antibodies by the radioimmunoassay technique described above for the detection of anti-nDNA antibodies in a sample. The fraction containing the eluted anti-nDNA antibody was also shown to be enriched with 3I reactive anti-nDNA antibodies by the same radioimmunoassay technique. In addition, the eluted fraction was shown to have increased anti-DNA activity and the filtrate was shown to have decreased anti-nDNA activity by both a crithidia assay and by an enzyme linked immunosorbent assay (ELISA). Table II shows the optical density of the serum, the eluted fraction and the filtrate, each of which was contacted with free DNA. The optical density was measured at 405 nm, so that the reading corresponds to the amount of anti-nDNA antibody in the sample. As seen in Table II, for each of the patients the amount of anti-nDNA antibody is the greatest in the eluted fraction which contains the 3I reactive anti-nDNA antibodies and the lowest in the filtrate which is depleted of the 3I reactive anti-nDNA antibodies. As such, the serum has been successfully depleted of anti-nDNA antibodies by passage through the column.

TABLE II

|  | Serum | Eluted Fraction | Filtrate |
|---|---|---|---|
| MO | 0.348 | 1.004 | 0.198 |
| YC | 0.403 | 0.678 | 0.202 |
| NS | 0.160 | 0.370 | 0.134 |
| RaRe | 0.200 | 0.332 | 0.143 |
| RoRo | 0.184 | 0.310 | 0.120 |

A column formed with the antibodies of the present invention can specifically remove only the anti-nDNA antibodies from the serum of an SLE patient and may therefore eliminate the generalized immunosuppression caused by current SLE therapies involving removal of all antibodies. In addition, the column can deplete the serum of circulating immunocomplexes of anti-nDNA antibody and DNA if one uses the antibody of the present invention which is capable of reacting with a shared idiotypic determinant on human anti-nDNA antibody which is located outside the DNA binding region. This is especially important as it is known that these immune complexes are a major pathogenic component of disease in SLE patients. A column formed with the antibodies of the present invention removes from the serum of SLE patients anti-nDNA present in immune complexes as well as monomeric anti-nDNA and as such is a desirable therapeutic modality for SLE patients.

As will be readily apparent to those skilled in the art, the invention may be used in other specific forms or for other purposes without departing from its spirit or central characteristics. The present embodiments are therefore to be considered as illustrative and not restrictive, the scope of the invention being indicated by the claims rather than by the foregoing description, and all embodiments which come within the range of equivalence of the claims are intended to be embraced.

What is claimed is:

1. A method for removing human anti-native DNA antibody from a liquid sample comprising contacting a liquid sample with a medium containing monoclonal, anti-idiotypic antibodies capable of binding to a shared idiotype on human anti-native DNA antibody, said idiotype shared between genetically nonidentical individuals, and separating said medium from said sample to remove the human anti-native DNA antibodies therefrom.

2. A method as in claim 1 in which said monoclonal antibodies are capable of reacting with a shared idiotype on human anti-native DNA antibody which is located outside the DNA binding site of the anti-native DNA antibody.

3. A method for removing human anti-native DNA antibody from a liquid sample comprising coupling monoclonal, anti-idiotypic antibodies capable of binding to a shared idiotype on human anti-native DNA antibody to a medium, said idiotype shared between genetically nonidentical individuals, contacting a liquid sample to said medium to permit binding of human anti-native DNA antibody in said sample to said anti-idiotypic antibodies and separating said sample from said medium to remove the human anti-native DNA antibodies therefrom.

4. A method as in claim 3 which further comprises eluting the bound anti-native DNA antibodies from said medium to permit reuse of said medium.

5. A method as in claim 3 in which said monoclonal antibodies are capable of reacting with a shared idiotype on human anti-native DNA antibody which is located outside the DNA binding site of the anti-native DNA antibody.

6. A method as in claim 3 in which said medium is a solid phase.

7. A method as in claim 6 in which said medium comprises sepharose.

8. A method as in claim 7 in which said monoclonal, anti-idiotypic antibody is coupled to said sepharose by treating said sepharose with cyanogen bromide.

9. A method as in claim 3 in which said monoclonal, anti-idiotypic antibodies are secreted by the hybridoma deposited at the American Type Culture Collection and catalogued as ATCC #HB 8376.

* * * * *